United States Patent
Manzke et al.

(10) Patent No.: US 7,648,273 B2
(45) Date of Patent: Jan. 19, 2010

(54) RADIATION SHIELDING FOR TOMOGRAPHIC SCANNERS

(75) Inventors: Roert M. Manzke, Cambridge, MA (US); Dirk Vananderoye, Bree (BE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/093,457

(22) PCT Filed: Oct. 30, 2006

(86) PCT No.: PCT/IB2006/054018

§ 371 (c)(1),
(2), (4) Date: May 13, 2008

(87) PCT Pub. No.: WO2007/060561

PCT Pub. Date: May 31, 2007

(65) Prior Publication Data

US 2009/0110152 A1     Apr. 30, 2009

Related U.S. Application Data

(60) Provisional application No. 60/597,318, filed on Nov. 23, 2005.

(51) Int. Cl.
*H01J 35/16* (2006.01)
(52) U.S. Cl. ............... 378/203; 378/195; 250/515.1
(58) Field of Classification Search .......... 378/4–20, 378/193–198, 203; 250/515.1
See application file for complete search history.

(56) References Cited

U.S. PATENT DOCUMENTS

| 4,977,585 | A | | 12/1990 | Boyd |
| 5,185,778 | A | * | 2/1993 | Magram ............... 378/196 |
| 2005/0173658 | A1 | | 8/2005 | Lemer |

FOREIGN PATENT DOCUMENTS

| EP | 1477992 A1 | 11/2004 |
| JP | 64056037 | 3/1989 |
| JP | 08262141 | 10/1996 |
| WO | 2005102174 A1 | 11/2005 |

OTHER PUBLICATIONS

Vano, et al., "Lens Injuries Induced by Occupational Exposure in Non-optimized Interventional Radiology Laboratories, The British Journal of Radiology," Jul. 1998, pp. 728-733.
Nawfel, et al., "Patient and Personnel Exposure during CT Flouroscopy-guided Interventional Procedures," Radiology, Jul. 2000, 216(1), pp. 180-184, RSNA.

(Continued)

*Primary Examiner*—Courtney Thomas

(57) ABSTRACT

A radiation shield (24) for use with a tomographic scanner (10) provides a shielded region which at which a clinician or other person is shielded from radiation generated during a scan of a patient. A support (20) supports the first radiation shield (24) in a location near the scanner (10). The shield support (20) may be attached to the scanner (10).

23 Claims, 9 Drawing Sheets

OTHER PUBLICATIONS

Bashore, MD, et al., "American College of Cardiology/Society for Cardiac Angiography and Interventions Clinical Expert Consensus Document on Cardiac Catheterization Laboratory Standards," Journal of the American College of Cardiology, 2001, 37(8), pp. 2170-2214, Elsevier Science Inc.

Kuon, et al., "Radiation Exposure in Invasive Cardiology—An Ongoing Challenge for Cardiologists, Industry and Control Organs," Business Briefing: Global Healthcare, 2002, pp. 55-58.

Philips, Mobile C-arm System BV Pulsera, 2003, 12 pages, Koninklijke Philips Electronics N.V., The Netherlands, www.medical.philips.com.

Reek, Dr. Christine, "Radiation Protection on Cardiac and Interventional Procedures," CR/IRPA, May 2004, pp. 1-14.

Fluke Biomedical, Radiation Safety Catalog, 2005, 22 pages, Fluke Corporation, www.flukebiomedical.com/rms.

* cited by examiner

RADIATION SHIELDING FOR TOMOGRAPHIC SCANNERS

CROSS REFERENCE TO RELATED APPLICATIONS

This application claims the benefit of U.S. provisional application Ser. No. 60/597,318 filed Nov. 23, 2005, which is incorporated herein by reference.

The present application relates to radiation shielding. It finds particular application to the shielding of personnel from x-rays generated during a computed tomography (CT) scan. It also finds application to the shielding of personnel and objects from ionizing radiation generated during other tomographic examinations.

CT scanners have proven to be invaluable sources of information indicative of the internal structure of an object. In medical imaging, for example, CT scanners are widely used to provide images and other information about the physiology of human patients.

CT scanners typically include a radiation source such as an x-ray tube. Due to scattering and other phenomena, however, radiation is typically present in the general vicinity of the scanner during a scan.

As a result, the scanner's operating console is often located in a separate room. The two rooms are typically separated by a shielded wall, which often includes an optically transparent window fabricated from a radiation attenuative material such as leaded glass. An intercom system is sometimes used to allow voice communication between the operator or clinician and the patient. While such an arrangement protects the clinician from repeated exposure to radiation and allows limited verbal and visual communications, it can present a physical and psychological barrier between the clinician and patient, even during routine radiological examinations. This barrier can have a deleterious effect on the patient's experience, especially in pediatric and other cases where the patient may benefit psychologically from the proximity to the clinician, in emergency or trauma situations, or in other situations where convenient physical access to the patient is desirable.

CT scanners have also been used in various interventional applications. As a result of ongoing technological advances, the use of CT in interventional applications is likely to increase. As just one example, CT fluoroscopy and dynamic three dimensional imaging may significantly improve catheter navigation and placement in cardiac procedures. Interventional applications typically require one or more clinicians—one example being an interventionist and an anesthesiologist—to be within arm's length of the patient during the procedure. Again, it is generally undesirable for the clinicians to be repeated exposed to radiation generated during multiple procedures.

These situations have been addressed by the use of lead aprons and other shielded clothing. However, such clothing is typically heavy, bulky, and uncomfortable, especially when repeatedly taken on and off or worn for significant periods of time. Such clothing often provides shielding only for limited portions of the operator's body.

Portable shielded partitions have also been used. These partitions can typically be wheeled or otherwise moved from room to room and positioned between the clinician and the scanner. However, these partitions are typically heavy and unwieldy, and their portability can be constrained by the presence of personnel, other equipment and its associated cabling, and the like. These partitions can also present a physical and physiological barrier between the clinician and the patient.

Still others have proposed scanner mounted shielding arrangements for use with CT scanners. See U.S. Pat. No. 4,977,585 entitled Self Shielded Computerized Tomography Scanner to Boyd; Japanese Patent Publication No. 64-056037 entitled X-ray CT Apparatus to Yasuo. Nonetheless, there remains substantial room for improvement.

Aspects of the present invention address these matters, and others.

According to one aspect of the present invention, an apparatus is for use with a tomographic scanner having a patient support which supports a patient in an examination region during a scan. The apparatus includes a first radiation shield and a shield support which supports the first radiation shield for horizontal movement along a path transverse to the object support. The first radiation shield is movable to at least a first position at which the first radiation shield provides a first location in the vicinity of the scanner at which a human is shielded from radiation generated during a scan of the patient.

According to another aspect of the invention, an apparatus for use with a tomographic scanner includes an arcuate first radiation shield which subtends an arc about a vertical axis. The apparatus also includes a support which supports the first radiation shield in a location near the scanner. The first radiation shield includes a transparent shield portion. The first radiation shield defines a shielded region in which a human is shielded from radiation generated during a scan.

According to another aspect of the present invention, an apparatus is for use with a tomographic scanner including a gantry and a patient support. The apparatus includes a first radiation shield which defines a first patient receiving aperture, a second radiation shield which defines a second patient receiving aperture, and a support which supports the first radiation shield and the second radiation for horizontal motion along a path adjacent a face of the gantry and transverse to the patient support. The first radiation shield is located on a first transverse side of the patient support, and the second radiation shield is located on a second transverse side of the patient support.

According to another aspect of the present invention, an apparatus for use with a tomographic scanner includes a first radiation shield and a support which supports the first radiation shield in a location adjacent the scanner. The support supports the radiation shield for pivotal motion to at least a first position which provides a location in the vicinity of the scanner at which a human is shielded from radiation generated during a scan of the patient.

Those skilled in the art will appreciate still other aspects of the present invention upon reading an understanding the attached figures and description.

The present invention is illustrated by way of example and not limitation in the figures of the accompanying drawings, in which like references indicate similar elements and in which.

Figure 1:
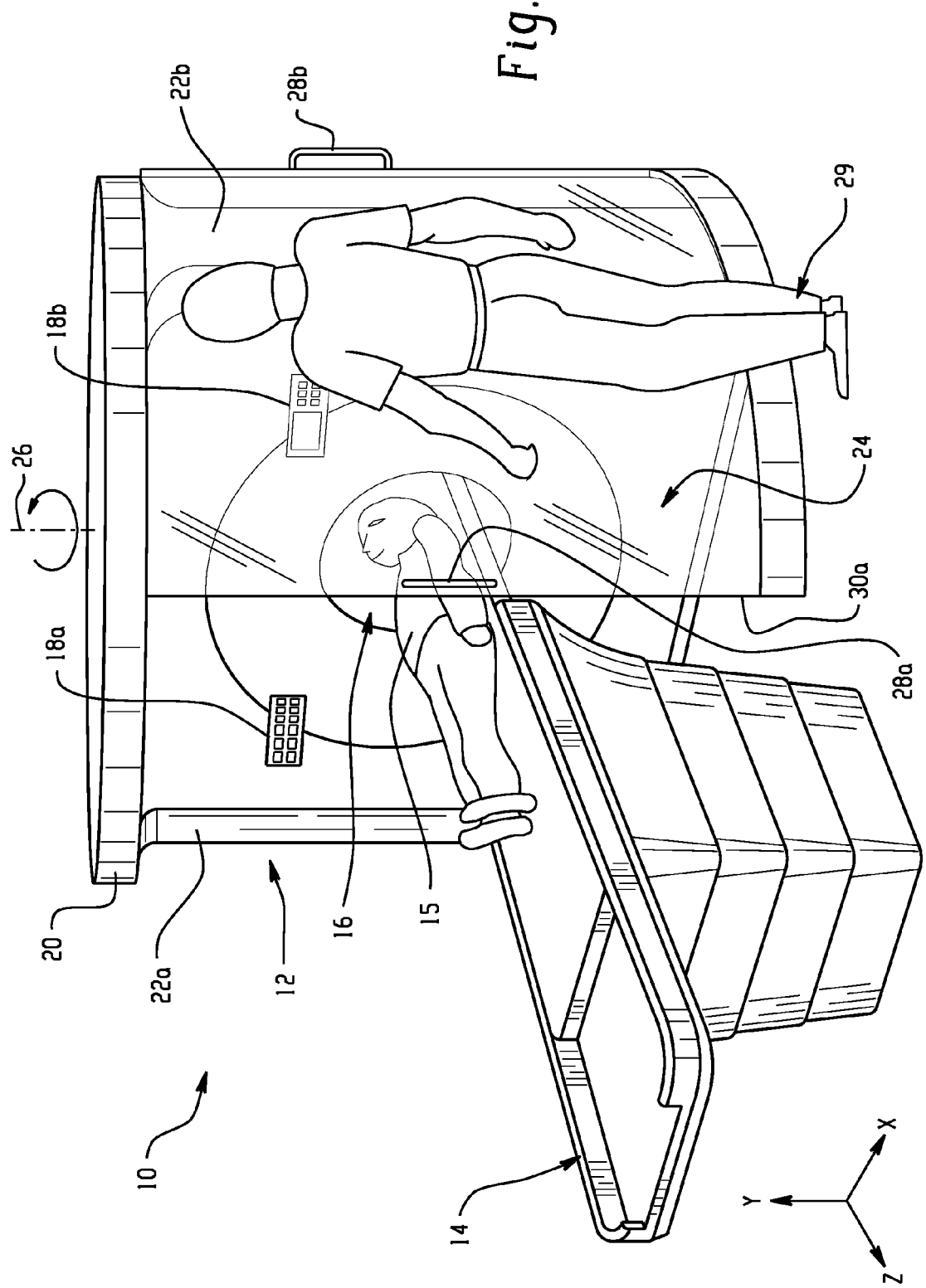
FIG. 1 is a perspective view of a CT scanner having an arcuate radiation shield.

With reference to FIG. 1, a CT scanner 10 includes a gantry 12 and patient support 14. Disposed in the gantry are a radiation source such as an x-ray tube and radiation sensitive detectors which detect radiation which has traversed an examination region 16. In a third generation scanner, the x-ray source and detectors rotate about the examination region 16. The gantry 12 may also be tiltable about the y-axis. The patient support 14 supports a human patient 15 or other object to be imaged in the examination region 16, and is preferably movable along the longitudinal or z and the vertical or y axes. Depending on the requirements of a particular scan protocol, a controller associated with the scanner 10 coordinates the motion of the patient support 14 during the scan. The scanner 10 typically also contains controls which allow manual operation of the patient support 14. Gantry-mounted operator controls 18a, 18b such as a keypad and display allow limited operation of the scanner 10 from a location proximate the gantry 12.

Figure 2:
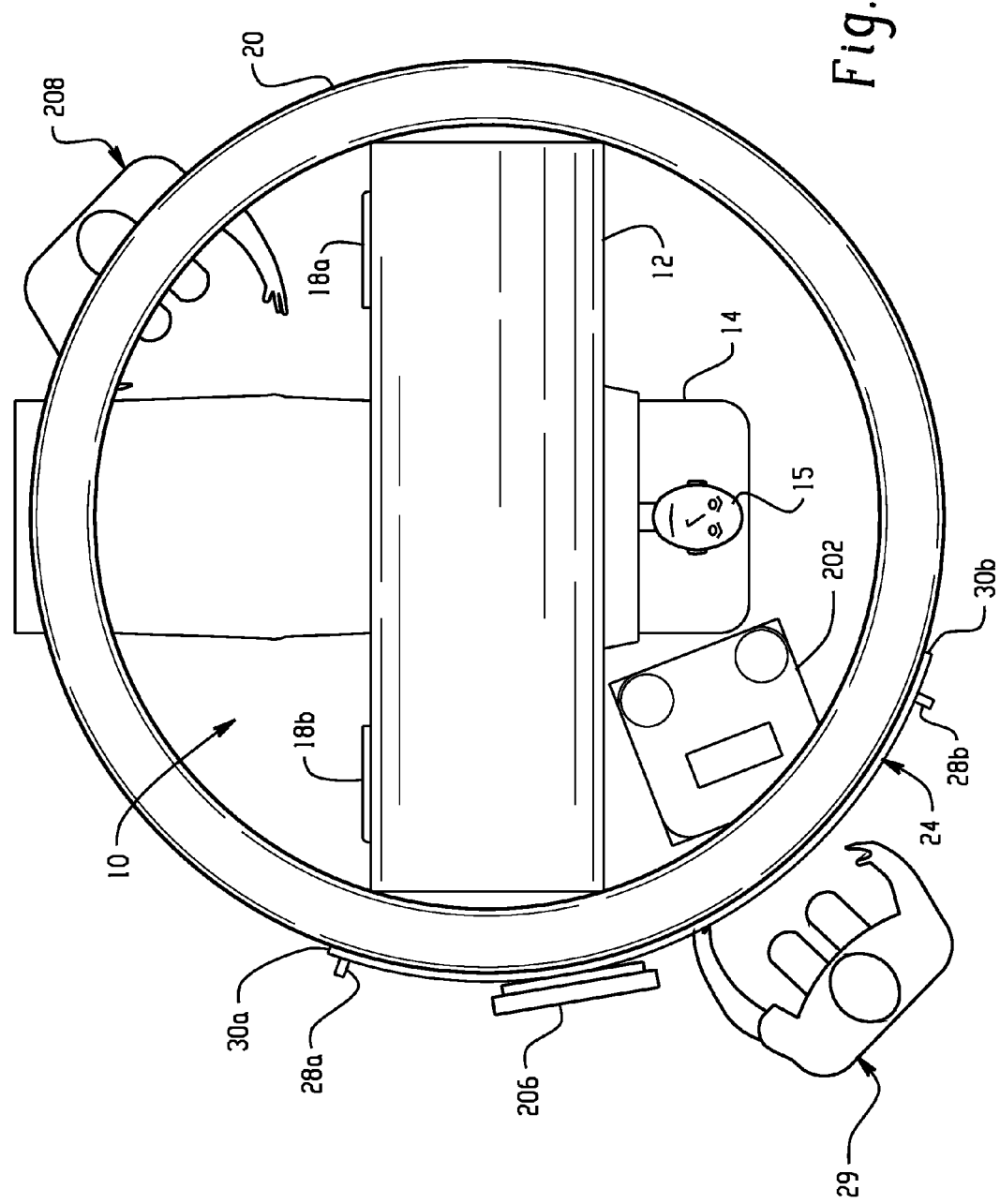
FIG. 2 is a top view of a CT scanner having an arcuate radiation shield.

With reference to FIGS. 1 and 2, a generally circular support 20 is supported by way of first 22a and second 22b floor supported vertical members. The vertical members 22a, 22b are also attached to gantry 12, so as to allow tiltable motion of the gantry 12 independent from the vertical members 22a, 22b and support 20.

An arcuate radiation shield 24 is in turn movably mounted to the circular support 20 by way tracks or rails for movement in an arcuate path in a direction transverse to the object support 14. The arcuate motion is centered on an axis of rotation 26 which intersects the center of the examination region 16. Some or all of the shield's weight may also be supported by wheels or rollers which contact the floor. The shield 24 is movable though a range of motion which is limited primarily by the patient support 14. Other ranges of motion may be also be implemented.

In one embodiment, the shield includes one or more handles 28a, 28b which facilitate manual movement of the shield 24 by the clinician 29 or other operator. The shield 24 may also be driven by a motor other actuator, with motion controlled by clinician operated switches located at the handles 28a, 28b or other convenient location. To prevent inadvertent motion, the switches may require two-handed operation. Proximity switches located at the edges 30a, 30b of the shield disable motion if the shield contacts a person or object in it the shield's path.

The shield 24 is fabricated from an optically transparent radiation attenuative material such as a clear leaded plastic, the material and thickness of which is selected to provide a 0.5 mm lead equivalent other desired shielding. It should be understood that the optically transparent material need not be perfectly transparent and may also, for example, be tinted. In addition, some or all the bottom, sides, or other desired portion of the shield 24 may also be fabricated from a substantially opaque material. The shield 24 may also be fabricated from multiple pieces of transparent material, and the transparent portion of the shield 24 may also take the form of a window. Where optical transparency is not required, the shield 24 may also be implemented by way of a lead lined vinyl curtain movably suspended from the support 20. In the illustrated embodiment, the shield 24 has dimensions on the order of 2 meters by 1 meter, and the support 20 has a radius of about 1 meter, although other dimensions may be implemented.

FIG. 1 depicts the shield 24 in a first position located nearer to the front of the scanner 10. As shown, the shield provides a shielded area in which an operator or clinician 29, family member, or other person can be situated during a scan. The corresponding portion of the floor may also be painted or marked in a contrasting color, outlined, fabricated in a different color or type of floor material, or the like to assist in identifying the safe zone. Lighting disposed in the surface of the floor or a projection may also be activated to indicate the shielded area when the shield 24 is appropriately positioned.

Figure 3:
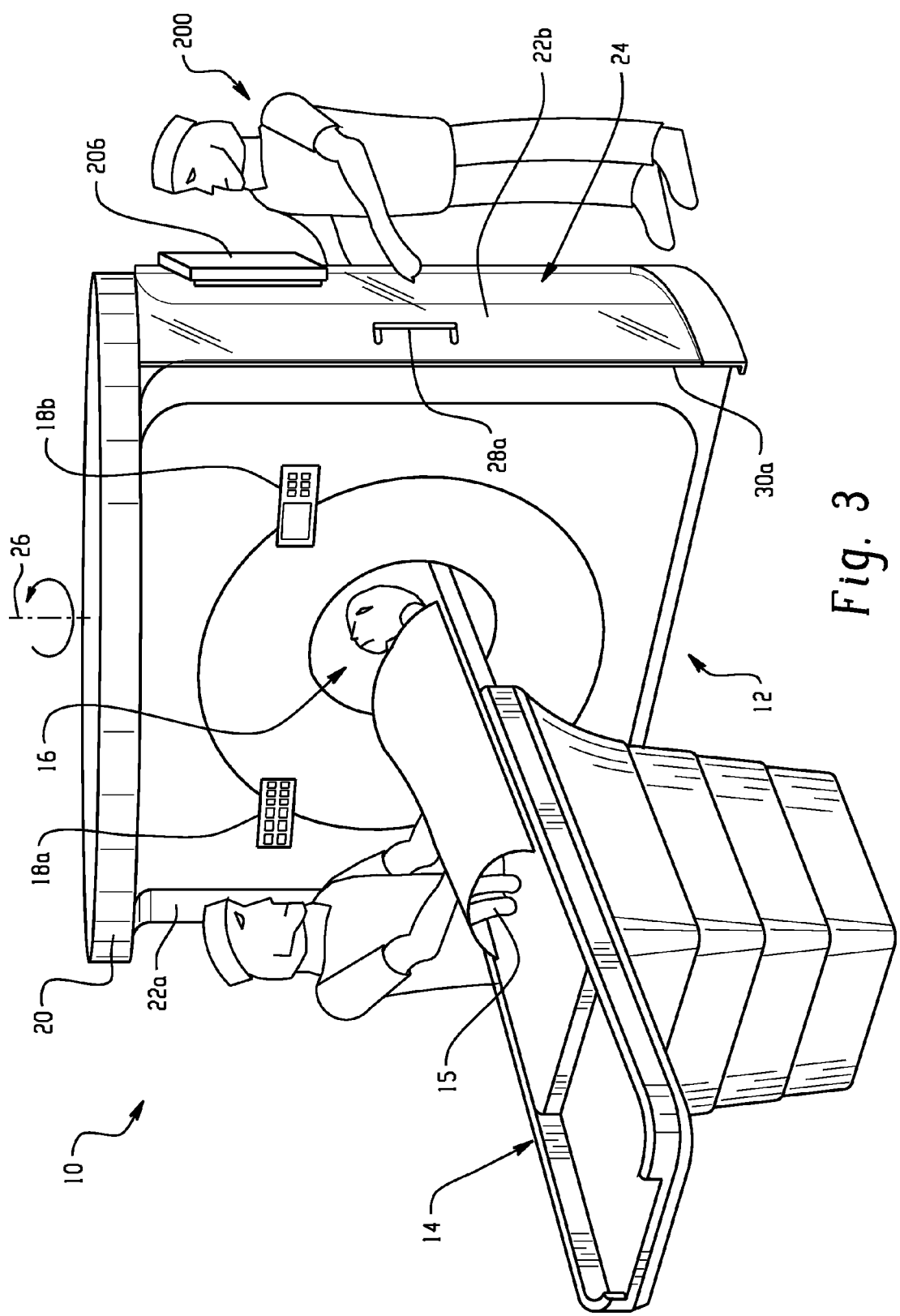
FIG. 3 is a perspective view of a CT scanner having an arcuate radiation shield.

FIGS. 2 and 3 depict the shield 24 in a second position located nearer to the rear of the scanner 10. As depicted, an exemplary anesthesiologist 200 is located behind the shield 24, with the anesthesiologist's equipment 202 located in the space between the shield 24 and the gantry 12. An exemplary second clinician 208 or interventionist is depicted as being located even nearer to the patient 15. In the course of a scan, the second clinician 208 would preferably be wearing shielded garments or otherwise be shielded. FIGS. 2 and 3 also depict a human readable display 206 mounted to the shield 24 for movement therewith. Required electrical connections and cabling are provided through the support 20. The shield 24 may also carry controls analogous to controls 18a, 18b. The display 206 may also be mounted at a location between the gantry 12 and the shield 24, for example in the general vicinity of the controls 18a, 18b.

To provide additional flexibility, the scanner 10 may also include second or additional shields analogous to the first shield 24. In one embodiment, the additional shield or shields are mounted concentrically with the first shield 24 so that the each is movable about the full range of motion. In another embodiment, each shield may have a more limited range of motion. In addition, one or more of the first 24 or additional shields (if any) may be located in a fixed position.

Figure 4:
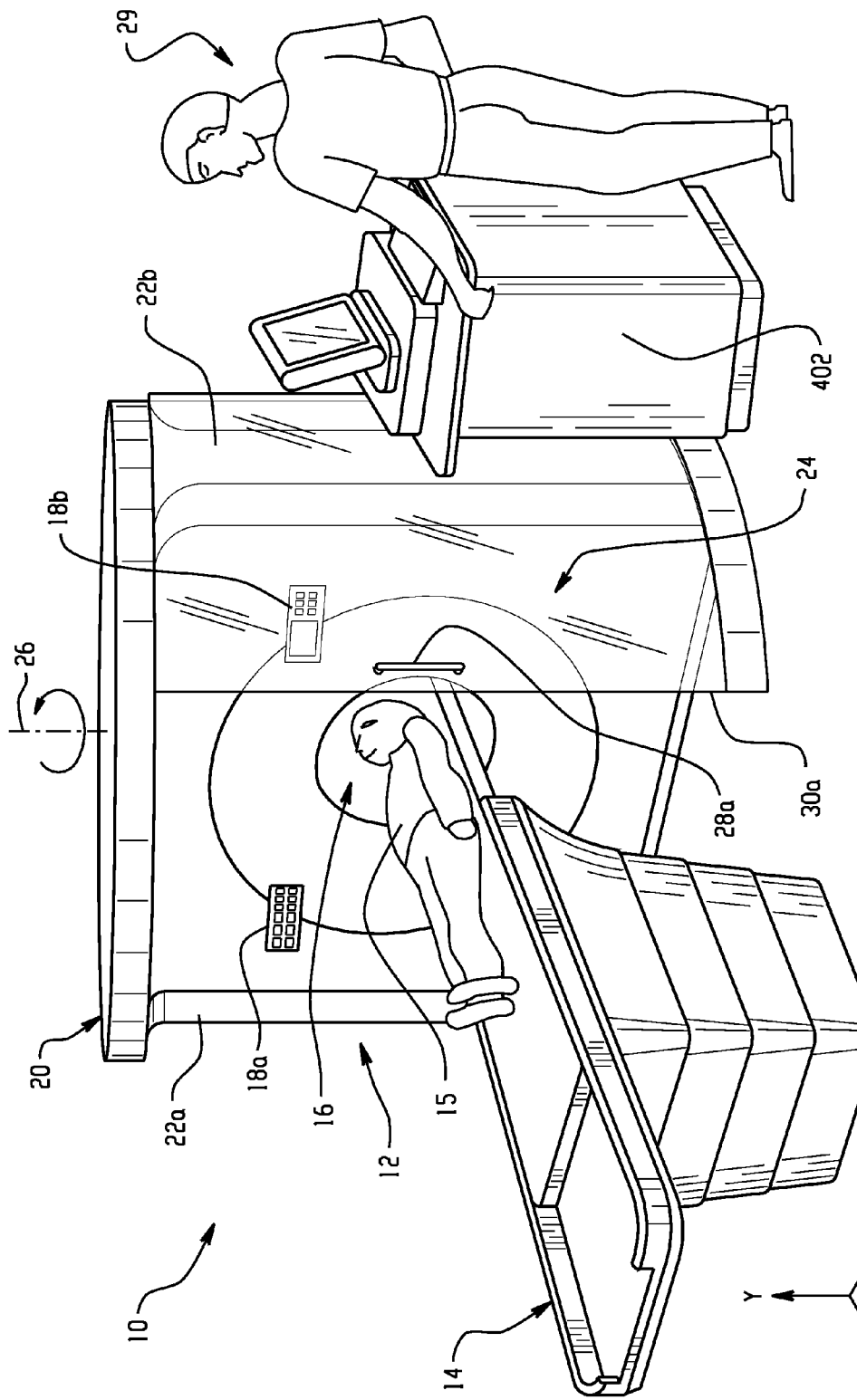
FIG. 4 is a perspective view of a CT scanner having an arcuate radiation shield.
Figure 5:
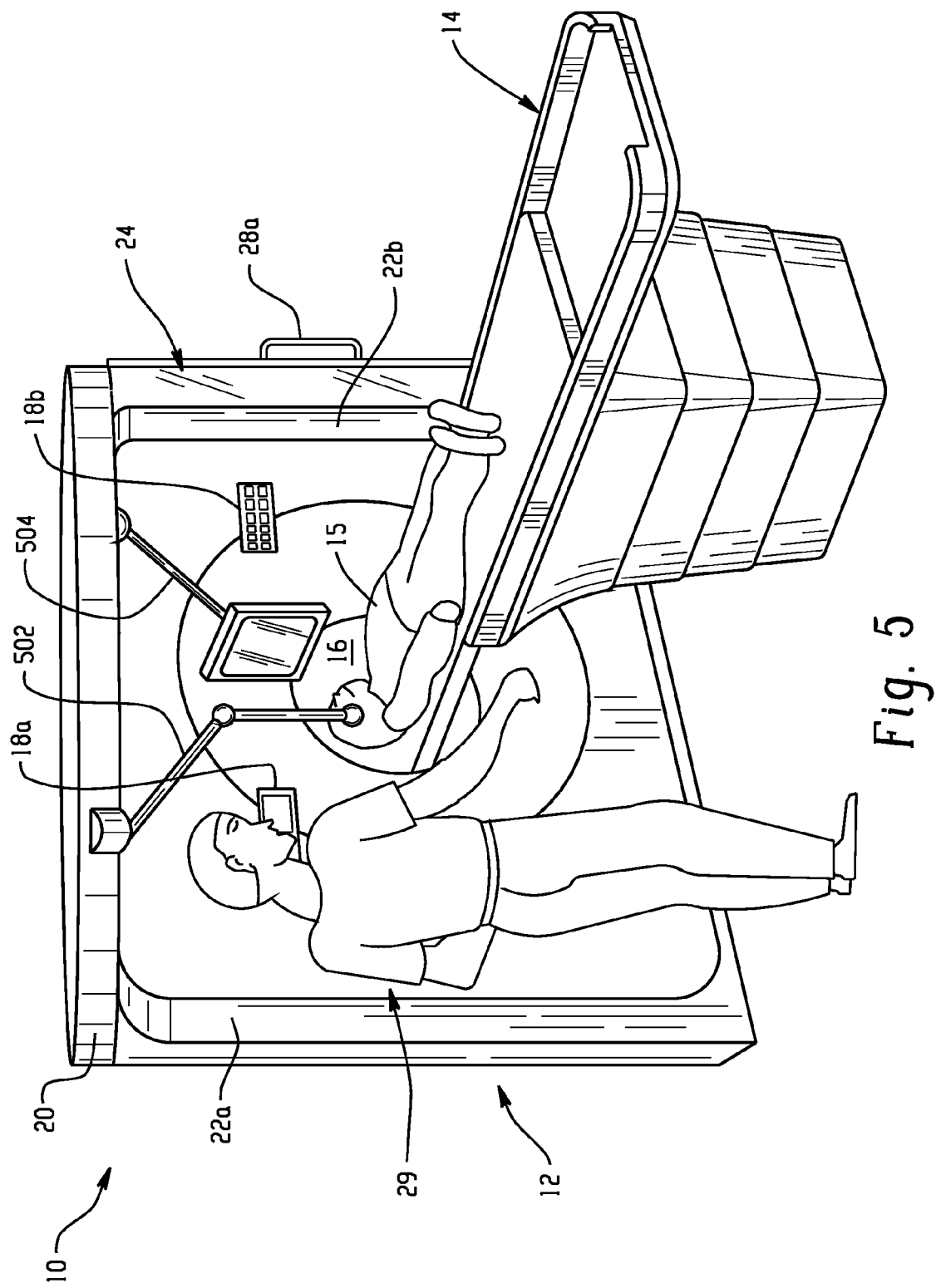
FIG. 5 is a perspective view of a CT scanner having an arcuate radiation shield.

With reference to FIG. 4, the scanner's operator console computer 402 may be positioned so that operator 29 is located behind the shield 24. In addition, the support 20 may carry additional devices such as an articulated arm 502 and display 504 used in interventional procedures.

Figure 6:
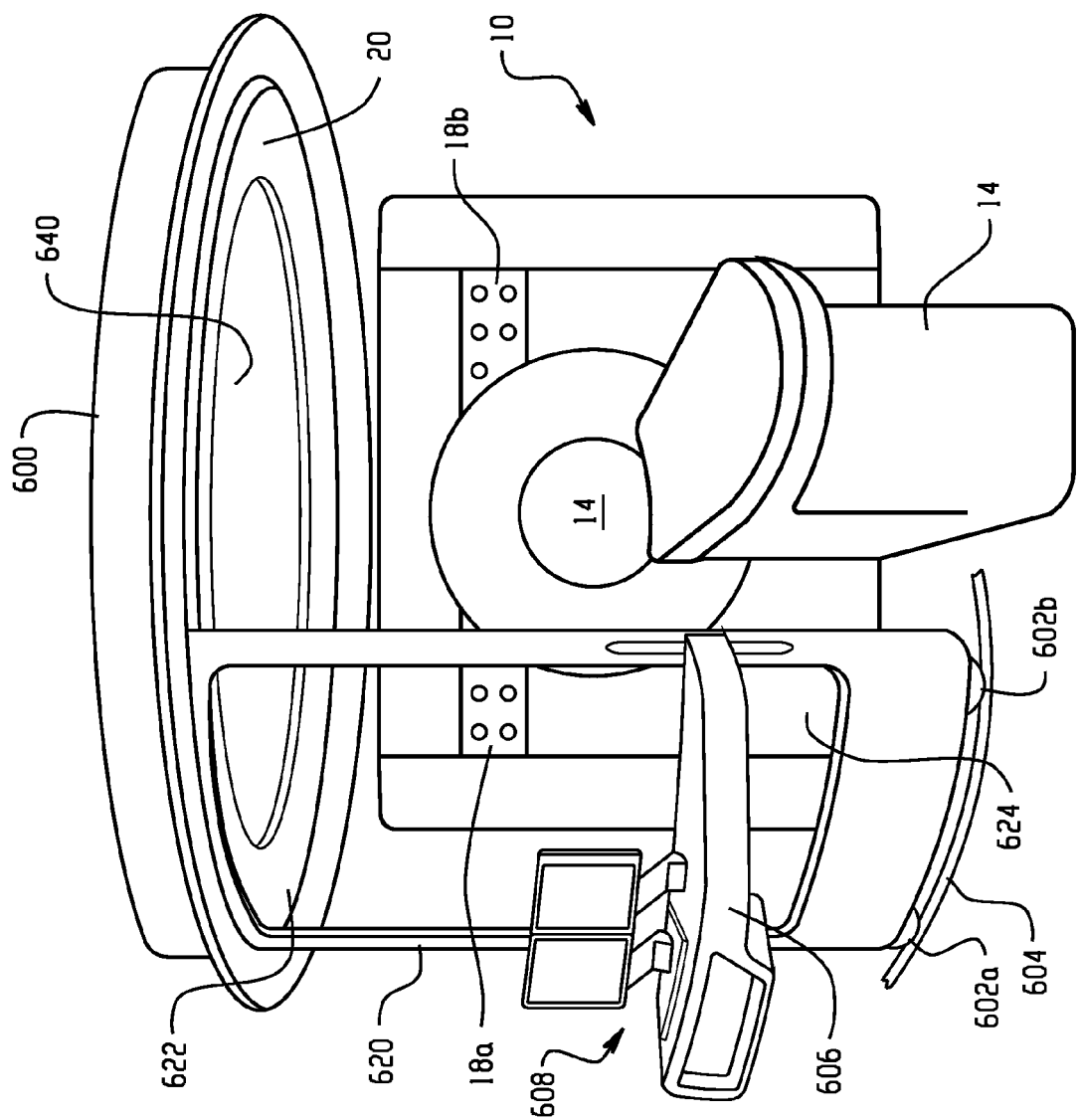
FIG. 6 is a perspective view of a CT scanner having an arcuate radiation shield.

FIG. 6 depicts halo structure 600 which is supported by the ceiling or other suitable overhead support structure. Associated with the halo 600, the support 20 is likewise supported by the ceiling or other overhead structure. Together with optional wheels or rollers 602a, 602b which help support the shield 24 for movement in a floor mounted track or railing 604, the support 20 supports the shield 24 for motion about the axis 26. As illustrated, the shield 24 includes a frame 620 and upper 622 and lower 624 shield portions. In one embodiment, both the upper 622 and lower 624 shield portions are optically transparent. In another, the lower shield portion 624 is optically opaque. Also as illustrated, a shelf or table 606 is carried by the shield 24 for movement therewith. Some or all of the operator's console 608 may also be mounted to the shield 24 for movement therewith, as may be a seat of stool for use by the clinician.

Lighting, speakers, or a projection surface for displaying videos, photographs, or other materials which enhance the patient experience or facilitate communications with the patient may also be provided. Fluorescent or other lighting associated with the halo 600 provides indirect lighting in the region of the scanner 10. Task or other direct lighting may also be provided. In another embodiment, lighting may be disposed behind a translucent surface 640 at the interior region of the halo 600. The surface 640 may also serve as a projection surface for displaying videos and the like.

As will be appreciated, the overhead supported configuration of FIG. 6 is relatively independent of the scanner 10.

While such a configuration may be optimized for use with a particular model of scanner 10 or family of scanners, it is also particularly well suited for implementation as an optional accessory for use with a variety of different scanner models or families. As will also be appreciated, the various items and features discussed in connection with the scanner 10 supported configurations of FIGS. 1 through 5 may be juxtaposed with those of the ceiling supported configuration of FIG. 6, and vice versa, depending on the requirements of a particular application.

Figure 7:
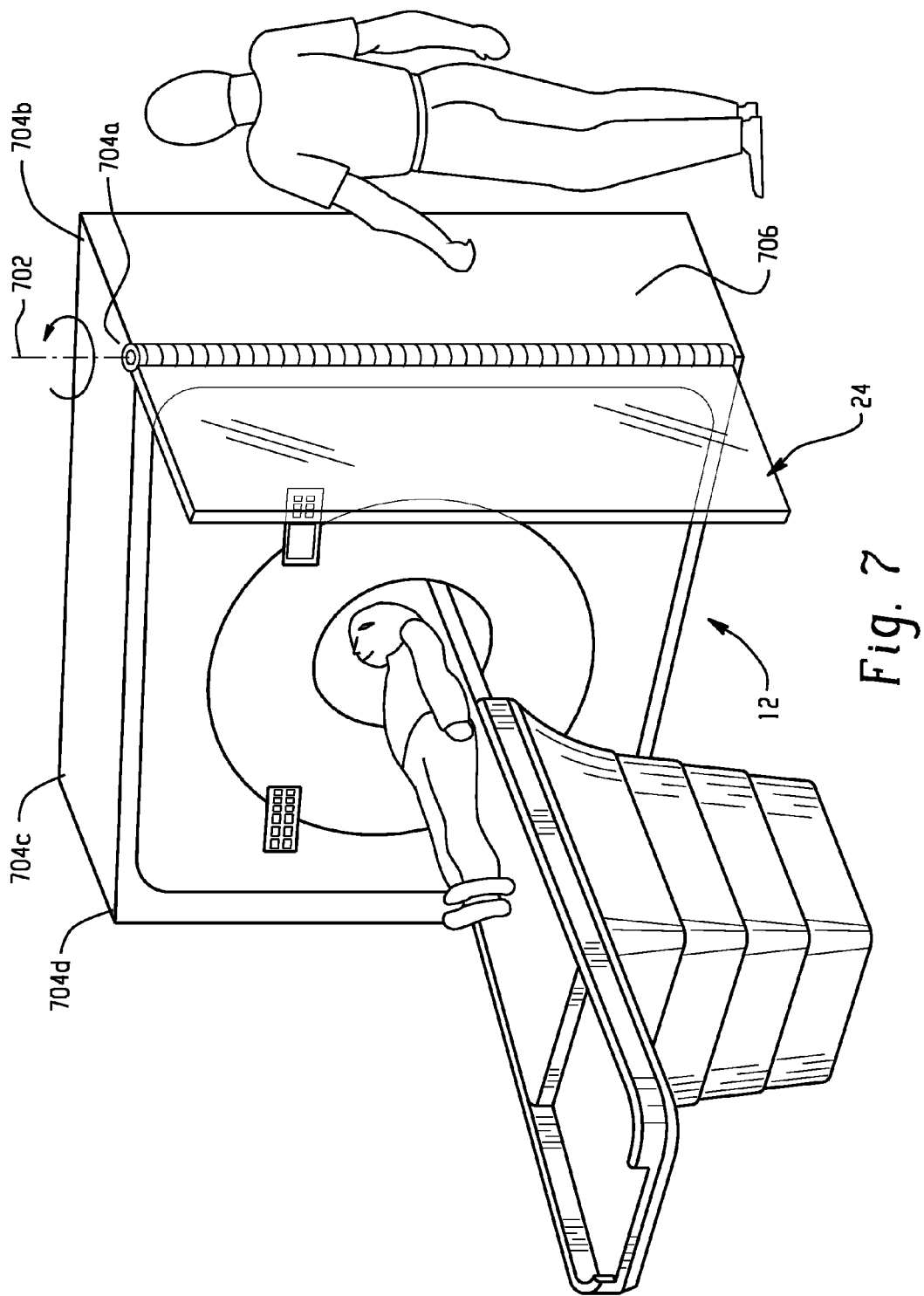
FIG. 7 is a perspective view of a CT scanner having a pivotally mounted radiation shield.
Figure 8:
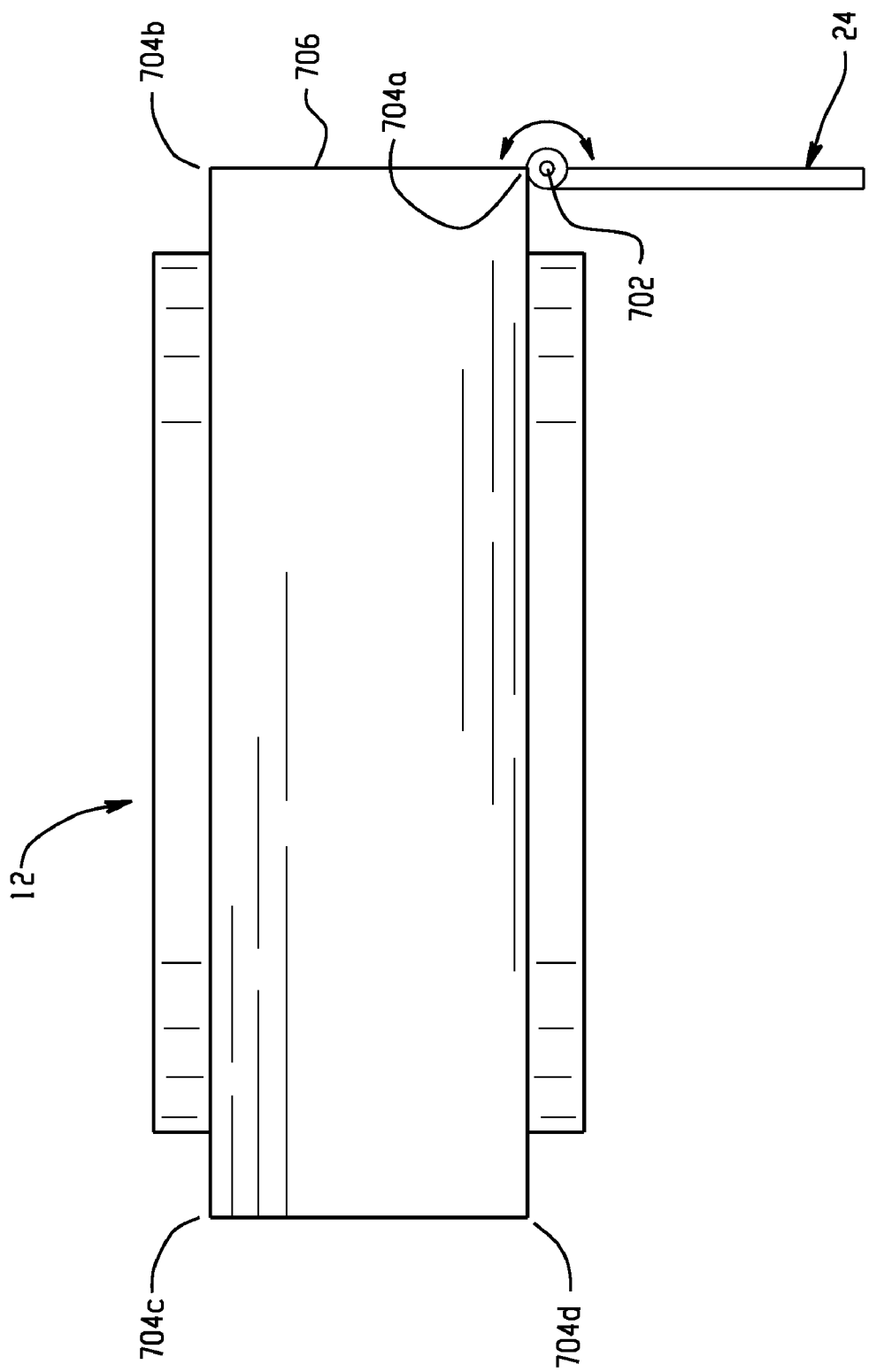
FIG. 8 is a top view of a CT scanner having a pivotally mounted radiation shield.

FIGS. 7 and 8 depict an alternate shield 24 configuration which provides pivotal motion of one or more shields 24. Where the gantry 12 provides tiltable motion, the shield 24 is preferably mounted to a stationary portion of the gantry so that tilting of the gantry 12 does not cause a corresponding movement of the shield 24. The shield 24 is pivotally mounted to the gantry 12 for motion about a pivot axis 702 at a location near a corner of the gantry 12 generally noted as 704a. One more shields 24 may also be located at corresponding locations generally noted as 704b, 704c, and 704d. Pivotal motion of the shield 24 allows a person standing behind the shield 24 to move closer to or further from the patient as desired. The shield 24 may also be pivoted to a position adjacent a side 706 of the gantry 12 when not in use. As will also be appreciated, the shield 24 may also pivotally mounted to the ceiling of other overhead support, to the floor, or both.

Figure 9A:
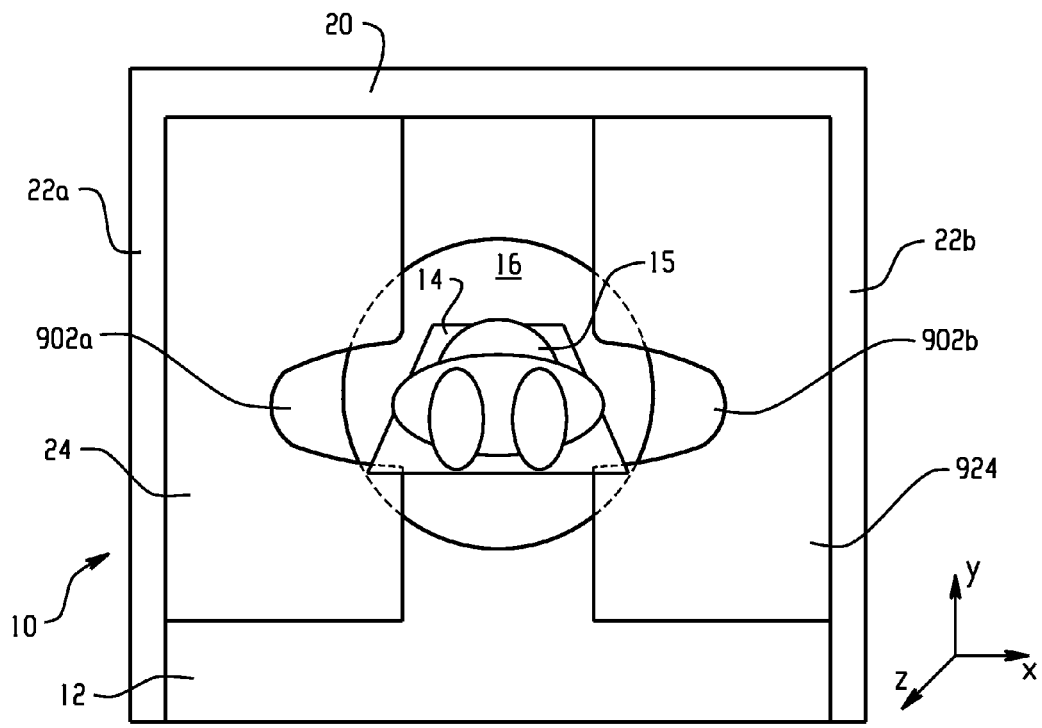
FIGS. 9a and 9b depict a CT scanner having first and second radiation shield portions.
Figure 9B:
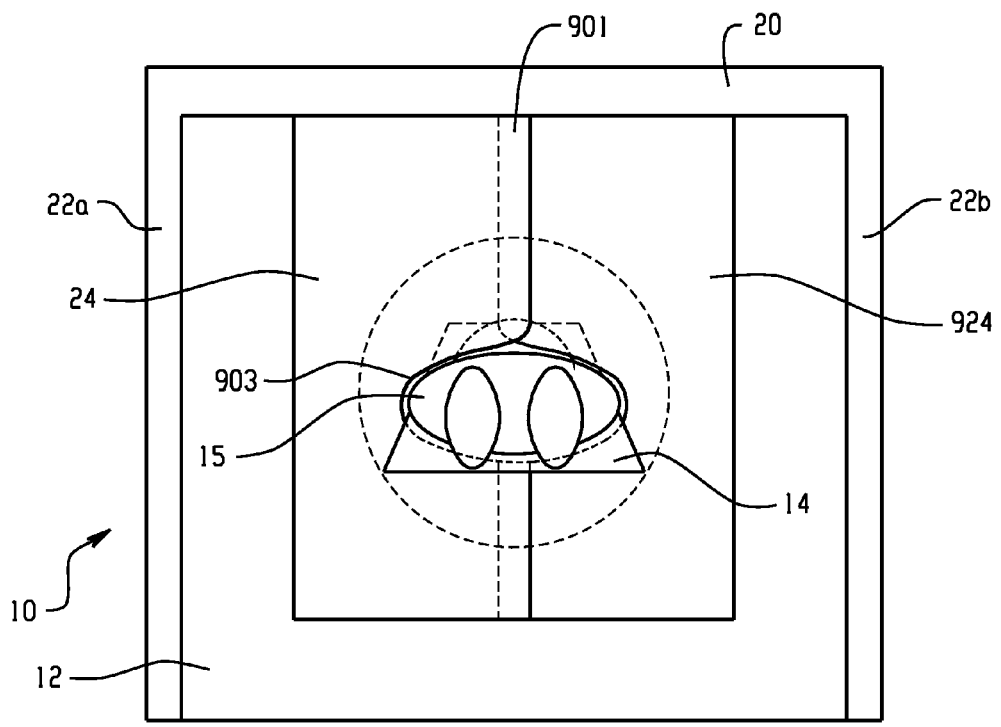

FIGS. 9a and 9b depict an arrangement in which first 24 and second 924 shields are positioned on either side of the patient support 14. The shields 24, 924 are suspended from the support 20 for linear movement toward and away from the patient support 14 in the transverse or x direction. The shields 24, 924 may also be supported by a lower track or rail or by wheels or rollers which contact the floor. The support 20 may also be supported by the ceiling or other overhead structure. The support 20 is positioned in relation to the gantry 20 so that the shields 24, 924 are located near the surface of the gantry 12, but having a gap which allows the shields 24, 924 to move without interference from the gantry 12. FIGS. 9a and 9b depict the shields in an open and a closed position; respectively. The shields 24, 924 are preferably offset slightly in the longitudinal or z-direction to allow an overlap 901 when closed. The shields 24, 924 may also be pivotally mounted to the gantry or an external structure as discussed generally above in relation to FIGS. 7 and 8.

Each shield 24, 924 defines respective patient receiving apertures 902a, 902b. The patient receiving apertures 902a, 902b are sized so that when closed, the shields 24, 924 define a patient aperture 903 which is slightly larger than the cross section of a patient 15 having a desired maximum size. The apertures 902a, 902b are also positioned to clear the underside of the patient support 14, which may also be provided with a shielding flange which provides an overlap analogous to that of the overlap 901.

In one embodiment, the shields 24, 924 are fabricated from a substantially rigid radiation attenuative material, and may, if desired, be optically transparent. The portion of the shields 24, 924 near the patient receiving apertures 902a, 902b, may also be fabricated from a flexible radiation attenuative material such as a lead lined vinyl of the sort used to fabricate curtains or garments. In that case, the patient receiving apertures 902a, 902b may be sized to define a patient aperture 903 which is slightly smaller than the cross section of the patient 15. The resulting overlap between the flexible portion of the shields 24, 924 and patient 15 provides improved shielding in the region of the shield 24, 924 patient interface.

To simplify opening and closing, the shields 24, 924 may also be provided with fasteners such as straps or ties, hook and loop fasteners, buttons, snaps or the like which are used to hold the flexible shield portions in a retracted position as needed. Once the patient 15 and shields 24, 924 are suitably positioned, the flexible shield portions are positioned against the patient.

The flexible shield portions may also be removably attached to the shields 24, 924 so as to facilitate removal and replacement by a clinician or operator. To provide additional flexibility for shielding patients of varying dimensions, the flexible shield portions may be provided in different sizes which define different sized patient apertures 903 and which can be selected and attached as desired. In still another embodiment, the removable shield portions may be fabricated from a rigid material and provided in different sizes which can be selected based on the dimensions of the patient. As will appreciated, the removable shield portions may be cleaned or after use. The shield portions themselves may also be disposable; disposable sterile covers may also be provided. Such an arrangement is especially beneficial where for portions of the shield located near the sterile field in an interventional procedure.

The portion of the shields 24, 924 near the patient receiving apertures 902a, 902b, may also be arranged in an iris or shutter like design. The shutter portions are preferably fabricated from flexible material and are positioned against the patient 15 as desired.

The shields may also be fabricated as flexible curtains or drapes. As will also be appreciated, the shields 24, 924 may also be fabricated as arcuate members and supported as discussed above in relation to FIGS. 1 through 6 above. The shields 24, 924 may also be mounted on first and second portable, wheeled partitions which can be positioned near the gantry 12 as desired.

While the above discussion has focused on shields 24, 924 located at the front of the gantry 12, analogous shields may also be provided at both the front and rear, or only at the rear of the gantry 12.

Of course, modifications and alterations will occur to others upon reading and understanding the preceding description. It is intended that the invention be construed as including all such modifications and alterations insofar as they come within the scope of the appended claims or the equivalents thereof.

The invention claimed is:

1. An apparatus for use with a tomographic scanner having a patient support which supports a patient in an examination region during a scan, the apparatus comprising:
   a first radiation shield;
   a stationary shield support which supports the first radiation shield for horizontal movement along a path transverse to the patient support, wherein the first radiation shield is movably affixed to the stationary shield support and is movable to at least a first position on the stationary shield support at which the first radiation shield provides a first location in the vicinity of the scanner at which a human is shielded from radiation generated during a scan of the examination region.

2. The apparatus of claim 1 wherein the shield support is arcuate and supports the first radiation shield for arcuate motion about a vertical axis.

3. The apparatus of claim 2 wherein the vertical axis interests a center of the examination region.

4. The apparatus of claim 1 wherein the scanner includes a gantry and wherein the shield support is attached to the gantry and disposed above the first radiation shield.

5. The apparatus of claim 1 wherein the shield support is adapted for mounting to a ceiling.

6. The apparatus of claim 2 wherein the apparatus includes a plurality of radiation shields supported for independent arcuate motion about the vertical axis.

7. The apparatus of claim 1 wherein the shield support supports an apparatus used in connection with an interventional medical procedure.

8. The apparatus of claim 1 wherein the first radiation shield carries a human readable display and/or an operating control for the scanner.

9. The apparatus of claim 2 wherein the scanner includes a gantry and wherein the first position is located at a front of the gantry and wherein the first radiation shield is movable to a second position at which the first radiation shield provides a second location in the vicinity of the scanner at which a human is shielded from radiation generated during a scan of the patient, and wherein the second position is located at a rear of the gantry.

10. The apparatus of claim 1 including a second radiation shield, and wherein the first radiation shield is supported for movement on a first side of the patient support and wherein the second radiation shield is supported for horizontal movement along a path transverse to the patient support on a side of the patient support opposite from the first side.

11. The apparatus of claim 10 wherein the first radiation shield defines a first patient receiving aperture and the second radiation shield defines a second patient receiving aperture.

12. The apparatus of claim 10 wherein the first and second radiation shields are movable relative to each other to a position at which the first and second radiation shields partially overlap.

13. The apparatus of claim 11 wherein the first a radiation shield includes a mechanically rigid shield portion and a mechanically flexible shield portion, and wherein the flexible shield portions is located adjacent the first patient receiving aperture.

14. The apparatus of claim 1 wherein the apparatus includes a plurality of selectively removable shield portions, and wherein the selectively removable shield portions define patient receiving aperture portions which receive patients of different sizes.

15. The apparatus of claim 1 wherein the first radiation shield is mounted for pivotal motion about a vertical pivot axis.

16. An apparatus for use with a tomographic scanner, the apparatus comprising:
   an arcuate first radiation shield which subtends an arc about a vertical axis, wherein the first radiation shield includes a transparent shield portion;
   a stationary support attached to a top surface of the tomographic scanner, wherein the stationary support movably suspends the first radiation shield in a location near the scanner, whereby the first radiation shield defines a shielded region in which a human is shielded from radiation generated during a scan.

17. The apparatus of claim 16 wherein the first radiation shield is located between the axis and the shielded region.

18. The apparatus of claim 16 wherein the support is adapted for mounting to an overhead structure.

19. The apparatus of claim 16 including means for providing a human perceptible indication of the shielded region.

20. An apparatus for use with a tomographic scanner including a gantry and a patient support, the apparatus comprising:
   a first radiation shield which defines a first patient receiving aperture, wherein the first radiation shield is located on a first transverse side of the patient support;
   a second radiation shield which defines a second patient receiving aperture, wherein the second radiation shield is located on a second transverse side of the patient support;
   a stationary support configured to move between at least a first location and a second location, wherein the stationary support movably supports the first radiation shield and the second radiation shield for horizontal motion from the at least first location to the at least second position along a path adjacent a face of the gantry and transverse to the patient support.

21. The apparatus of claim 20 wherein the first radiation shield includes a shield portion adjacent the patient receiving aperture which conforms to a cross section of a patient.

22. The apparatus of claim 20 wherein the support is adapted for mounting to a ceiling.

23. The apparatus of claim 20 including a selectively removable, sterile cover for covering the first radiation shield in a region near a sterile field in an interventional procedure.

* * * * *